(12) United States Patent
Culler

(10) Patent No.: US 6,342,479 B1
(45) Date of Patent: Jan. 29, 2002

(54) PROLONGING SURVIVAL OF TRANSPLANTED PANCREATIC CELLS

(75) Inventor: Michael D. Culler, Hopkinton, MA (US)

(73) Assignee: Societe de Counseils de Recherches et d'Applications Scientifiques, SAS, Paris (FR)

( * ) Notice: Subject to any disclaimer, the term of this patent is extended or adjusted under 35 U.S.C. 154(b) by 0 days.

(21) Appl. No.: 09/155,916

(22) PCT Filed: Apr. 8, 1997

(86) PCT No.: PCT/US97/05722

§ 371 Date: Mar. 1, 1999

§ 102(e) Date: Mar. 1, 1999

(87) PCT Pub. No.: WO97/37675

PCT Pub. Date: Oct. 16, 1997

(51) Int. Cl.$^7$ .............................................. A71K 38/08
(52) U.S. Cl. ............................ 514/16; 514/11; 514/12; 514/15; 514/17
(58) Field of Search ............................. 514/11, 15, 16, 514/17

(56) References Cited

U.S. PATENT DOCUMENTS

| 4,612,302 A | 9/1986 | Szabo et al. |
| 4,904,642 A | 2/1990 | Coy et al. |
| 5,538,739 A | 7/1996 | Bodmer et al. |

OTHER PUBLICATIONS

Database Medline. AN:L89160832. Szende et al. Proc. Natl. Acad. Sci USA, 86(5), 1643–1647, Mar. 1989.*
Database CaPlus, DN: 111:71271. Bilgen et al. Transplant. Proc., 1989, 21(1, Book 3), 2829–30.*
Steiner et al.; Somatostatin: Progress in Segmental Pancreas Transplantation. An Expert Mental Study of Canine Duct–Occluded Grafts; Transplant. Proc. (1984), 16(3) abstract.
Bjork et al., "Glucose Regulation of the Autoantigen GAD 65 in Human Pancreatic Islets", J. of Clinical Endocrinology and Metabolism 76:1574–1576, 1992.
Buhler et al., "Indications for Human Islet Transplantation: Chronic Pancreatitis and Cystic Fibrosis", Transplantation Proceedings 27:3148–3149, 1995.
Eizirik et al., "Prolonged Exposure of Human Pancreatic Islets to High Glucose Concentrations In Vitro Impairs the Beta–Cell Function", J. Clin. Invest. 90:1263–1268, 1992.
Grunt et al., "A Randomized Trial of a Somatostatin Analog for Preserving Beta Cell Function in Children With Insulin Dependent Diabetes Mellitus", Freund Publishing House Ltd. 7:331–334, 1994.
Kendall et al., "Pancreas and Islet Transplantation", The Endocrinologist 5:28–35, 1995.
Patel et al., "Subtype Selectivity of Peptide analogs For all Five Cloned Human Somatostatin Receptors (hsst 1–5)", Endocrinology 135:2814–2817, 1994.
Ponder et al., "Pancreatic Beta Cell Rest Induced by Use of Somatostatin Analog in Newly–Diagnosed Children and Adolescents With Type I Diabetes Mellitus", Metabolism & Diabetes p. 197A, 1168.
Pozo et al., "Endocrine Profile of a Long–acting Somotastatin Derivative SMS 201–995. Study in Normal Volunteers Following Subcutaneous Administration", Acta Endocrinologica 111:433–439, 1986.
Raynor et al., "Cloned Somatostatin Receptors: Identification of Subtype–Selective Peptides and Demonstration of High Affinity Binding of Linear Peptides", Molecular Pharmacology 43:838–844, 1993.
Reisine et al., "Molecular Biology of Somatostatin Receptors", Endocrine Reviews 16:427–442, 1995.
Robertson, R. Paul, "Pancreatic and Islet Transplantation for Diabetes—Cures or Curiosities?", Seminars in Medicine of the Beth Israel Hospital, Boston 327:1861–1868, 1992.
Rossowski et al., "Specific Inhibition of Rat Pancreatic Insulin or Glucagon Release by Receptor–Selective Somatostatin Anglogs", Biochemical & Biophysical Research Comm. 205:341–346, 1994.
Sandler et al., "Effects of Microtinamide Supplementation on Human Pancreatic Islet function in Tissue Culture", J. of Clin. Endocrinology and Metabolism 77:1574–1576, 1993.
Schuit et al., "Regulation of Adenosine 3', 5'–Monophosphate Levels in the Pancratic B Cell", Endocrinology 117:834–840, 1985.
Vlahos et al., "Diabetes Prevention in BB Rats by Inhibition of Endogenous Insulin Secretion", Metabolism 40:825–829, 1991.
Keen, Harry, "Insulin Resistance and the Prevention of Diabetes Mellitus", The New England Journal of Medicine 331:1226–1227, 1994.
Tolis et al., "Active Acromegaly: Selective and Non–Selective Effects on GH and Insulin Release . . . ", The Endocrine Society, 77th Annual Meeting Jun. 14–17, 1995, Washington, DC, Program & Abstract P3–118.
Williams, Gareth, "IDDM: Long Honeymoon, Sweet Ending", The Lancet 343:684–685, 1994.

* cited by examiner

Primary Examiner—Michael Borin
(74) Attorney, Agent, or Firm—Alan F. Feeney; Brian R. Morrill; Fish & Richardson

(57) ABSTRACT

A method of prolonging the survival of pancreatic cells transplanted in a patient. The method includes the step of administering a therapeutically effective amount of somatostatin or a somatostatin agonist to the patient.

16 Claims, No Drawings

PROLONGING SURVIVAL OF TRANSPLANTED PANCREATIC CELLS

This is a national stage entry (Aug. 5, 2001,MB) of International Patent Application No. PCT/US97/05722, with an international filing date of Apr. 8, 1997, now which claims priority to U.S. application Ser. No. 08/629,095, filed Apr. 8, 1996 now U.S. Pat. No. 5,686,418.

BACKGROUND OF THE INVENTION

Pancreas transplantation was developed as a treatment for Type I diabetes in 1966. Robertson, R. P., New Engl. J. Med. 327(26):1861 (1992). As a result of improved immunosuppression treatments, advances in surgical techniques, and enhanced availability of donors, the number of pancreas transplantations has increased since the later 1970s. The graft survival rate, however, still remains quite low, e.g., a one year survival rate of 72 percent and a three year survival rate of 54 percent. Kendall, et al., Pancreas and Islet Transplantation, The Endocrinologist 5:28–35 (1995). The suvival rate for islet cell transplantation is even lower wherein no patient has remained insulin-free for longer than one year. Diabetes 1993 Vital Statistics, pages 46–47 (American Diabetes Association, 1993).

SUMMARY OF THE INVENTION

The present invention relates to a method of prolonging the survival of transplanted pancreatic cells in a patient (e.g., a mammal such as a human). The method includes the step of administering a therapeutically effective amount of somatostatin or a somatostatin agonist to the patient. What is meant by "survival" is either the viability or the biological function (e.g., the insulin response to hyperglycemia) of the transplanted pancreatic cells. The somatostatin or somatostatin agonist may be administered parenterally, e.g., administered intravenously, subcutaneously, or by implantation of a sustained release formulation. The transplanted pancreatic cells may be a whole or partially intact pancreas, pancreatic islets, or isolated pancreatic cells. The cells may be autograft cells, allograft cells, or xenograft cells. In one embodiment, the patient is an insulin-dependent (e.g., Type I or late Type II diabetic).

Definition of "somatostatin agonist" will be defined below. A therapeutically effective amount depends upon the condition being treated, the route of administration chosen, and the specific activity of the compound used and ultimately will be decided by the attending physician or veterinarian. In one embodiment, the somatostatin agonist is administered to the patient during the pancreatic cell transplantation and continued until the transplanted cells have become established and fully functional in the patient. In another embodiment, the somatostatin agonist is administered for the lifetime of the cells (e.g., potentially the lifetime of the patient).

The somatostatin agonist may be injected parenterally, e.g., intravenously, into the bloodstream of the subject being treated. However, it will be readily appreciated by those skilled in the art that the route, such as intravenous, subcutaneous, intramuscular, intraperitoneal, enterally, transdermally, transmucously, sustained released polymer compositions (e.g., a lactide polymer or copolymer microparticle or implant), profusion, nasal, oral, etc., will vary with the condition being treated and the activity and bioavailability of the somatostatin agonist being used.

While it is possible for the somatostatin agonist to be administered as the pure or substantially pure compound, it may also be presented as a pharmaceutical formulation or preparation. The formulations to be used in the present invention, for both humans and animals, comprise any of the somatostatin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, somatostatin agonists in the cyclized form (e.g., internal cysteine disulfide bond) are oxidized; thus, the presence of reducing agents as excipients could lead to an opening of the cysteine disulfide bridge. On the other hand, highly oxidative conditions can lead to the formation of cysteine sulfoxide and to the oxidation of tryptophane. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering the solution sterile. The formulation may be presented in unit or multi-dose containers, for example, sealed ampoules or vials.

Formulations suitable for sustained release parenteral administrations (e.g., biodegradable polymer formulations) are also well known in the art. See, e.g., U.S. Pat. Nos. 3,773,919 and 4,767,628 and PCT Publication No. WO 94/15587.

The somatostatin or somatostatin agonist may also be administered with an immunosuppressive agent or insulin. Examples of immunosuppressive agents include cyclosporin, FK-506 glucocorticoids, and antibodies to T-cells.

Other features and advantages of the invention will be apparent from the following description of the preferred embodiments and from the claims.

Abbreviations

β-Nal=β-naphthylalanine
β-Pal=β-pyridylalanine
hArg(Bu)=N-guanidino-(butyl)-homoarginine
hArg(Et)$_2$=N,N'-guanidino-(dimethyl)-homoarginine
hArg(CH$_2$CF$_3$)$_2$=N,N'-guanidino-bis-(2,2,2,-trifluoroethyl)-homoarginine
hArg(CH$_3$, hexyl)=N,N'-guanidino-(methyl, hexyl)-homoarginine
Lys(Me)=N$^\epsilon$-methyllysine
Lys(iPr)=N$^\epsilon$-isopropyllysine AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle=norleucine
Nva=norvaline
Trp(Br)=5-bromo-tryptophan
Trp(F)=5-fluoro-tryptophan
Trp($NO_2$)=5-nitro-tryptophan
Gaba=γ-aminobutyric acid
Bmp=β-mercaptopropionyl
Ac=acetyl
Pen=pencillamine

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Somatostatin and Its Agonists

Somatostatin (somatotropin release inhibiting factor, or SRIF) has both a 14 amino acid isoform (somatostatin-14) and a 28 amino acid isoform (somatostatin-28). See Wilson, J. & Foster, D., *Williams Textbook of Endocrinology*, p. 510 (7th ed., 1985). The compound is an inhibitor of secretion of the growth hormone and was originally isolated from the hypothalamus. Brazeau et al., Science 179:77 (1973). Native somatostatin has a very short duration of effect in vivo since it is rapidly inactivated by endo- and exopeptidase. Many novel agonists have been prepared in order to enhance the duration of effect, biological activity, and selectivity (e.g., for the particular somatostatin receptor) of this hormone. What is meant by "somatostatin agonists" herein is a compound which (1) has a high affinity (e.g., Ki of less than 1 μM or, preferably, of less than 10 μM) for a somatostatin receptor (as determined by the receptor binding assay described below or any analogous assay), and (2) prolongs the survival of transplanted pancreatic cells (e.g., as determined by the biological assay described below or any analogous assay).

Various somatostatin receptors (SSTRs) have been isolated, e.g., SSTR-1, SSTR-2, SSTR-3, SSTR-4, and SSTR-5. Thus, the somatostatin agonist may be a SSTR-1 agonist, SSTR-2 agonist, SSTR-3 agonist, SSTR-4 agonist, or SSTR-5 agonist. One set of the somatostatin agonists to be used for practice the method of this invention are SSTR-5 agonists and SSTR-3 agonists. What is meant by an "SSTR-5 agonist" or an "SSTR-3 agonist" is a compound which (1) has a high affinity (e.g., Ki of less than 1 μM or, preferably, of less than 10 nM) for the SSTR-5 or SSTR-3, respectively (as defined by the receptor binding assay described below), and (2) prolongs the survival of transplanted pancreatic cells (e.g., as defined by the biological assay described below). The somatostatin agonist may also be selective for a particular somatostatin receptor, e.g., has a higher binding affinity for a particular somatostatin receptor subtype, e.g., an SSTR-5 or an SSTR-3 selective agonist.

Somatostatin agonists which can be used to practice the therapeutic method of the present invention include, but are not limited to, those covered by the formulae or those specifically recited in the publications set forth below, all of which are hereby incorporated by reference.

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13–19, 1992, Interlaken, Switzerland;
PCT Application WO 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979); and
U.S. Pat. No. 4,133,782 (1979).

Examples of somatostatin agonists include, but are not limited to, the following somatostatin analogs which are disclosed in the above-cited references:

D-β-Nal-Cys-Tyr-D-Trp-Lys-Thr-Cys-Thr-NH2;
D-Phe-Cys-Phe-D-Trp-Lys-Thr-Cys-β-Nal-NH2;
D-Phe-Cys-Tyr-D-Trp-Lys-Thr-Cys-β-Nal-NH2;
D-β-Nal-Cys-Phe-D-Trp-Lys-Thr-Cys-Thr-NH2;
D-Phe-Cys-Tyr-D-Trp-Lys-Thr-Pen-Thr-NH2;
D-Phe-Cys-Phe-D-Trp-Lys-Thr-Pen-Thr-NH2;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-ol;
H-D-Phe-Cys-Phe-D-Trp-Lys-Thr-Cys-Thr-$NH_2$;
H-D-Trp-Cys-Tyr-D-Trp-Lys-Val-Cys-Thr-$NH_2$;
H-D-Trp-Cys-Phe-D-Trp-Lys-Thr-Cys-Thr-$NH_2$;
H-D-Phe-Cys-Tyr-D-Trp-Lys-Val-Cys-Thr-$NH_2$;
H-D-Phe-Cys-Tyr-D-Trp-Lys-Val-Cys-Trp-$NH_2$;
H-D-Phe-Cys-Tyr-D-Trp-Lys-Val-Cys-Thr-$NH_2$;
Ac-D-Phe-Lys*-Tyr-D-Trp-Lys-Val-Asp-Thr-$NH_2$ (an amide bridge formed between Lys* and Asp);
Ac-hArg(Et)$_2$-Gly-Cys-Phe-D-Trp-Lys-Thr-Cys-Thr-$NH_2$;
Ac-D-hArg(Et)$_2$-Gly-Cys-Phe-D-Trp-Lys-Thr-Cys-Thr-$NH_2$;

Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$—CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
Bmp-Tyr-D-Trp-Lys-Val-Cys-Thr-NH$_2$;
Bmp-Tyr-D-Trp-Lys-Val-Cys-Phe-NH$_2$;
Bmp-Tyr-D-Trp-Lys-Val-Cys-p-Cl-Phe-NH$_2$;
Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo(Pro-Phe-D-Trp-N-Me-Lys-Thr-Phe);
cyclo(Pro-Phe-D-Trp-N-Me-Lys-Thr-Phe);
cyclo(Pro-Phe-D-Trp-Lys-Thr-N-Me-Phe);
cyclo(N-Me-Ala-Tyr-D-Trp-Lys-Thr-Phe);
cyclo(Pro-Tyr-D-Trp-Lys-Thr-Phe);
cyclo(Pro-Phe-D-Trp-Lys-Thr-Phe);
cyclo(Pro-Phe-L-Trp-Lys-Thr-Phe);
cyclo(Pro-Phe-D-Trp(F)-Lys-Thr-Phe);
cyclo(Pro-Phe-Trp(F)-Lys-Thr-Phe);
cyclo(Pro-Phe-D-Trp-Lys-Ser-Phe);
cyclo(Pro-Phe-D-Trp-Lys-Thr-p-Cl-Phe);
cyclo(D-Ala-N-Me-D-Phe-D-Thr-D-Lys-Trp-D-Phe);
cyclo(D-Ala-N-Me-D-Phe-D-Val-Lys-D-Trp-D-Phe);
cyclo(D-Ala-N-Me-D-Phe-D-Thr-Lys-D-Trp-D-Phe);
cyclo(D-Abu-N-Me-D-Phe-D-Val-Lys-D-Trp-D-Tyr);
cyclo(Pro-Tyr-D-Trp-t-4-AchxAla-Thr-Phe);
cyclo(Pro-Phe-D-Trp-t-4-AchxAla-Thr-Phe);
cyclo(N-Me-Ala-Tyr-D-Trp-Lys-Val-Phe);
cyclo(N-Me-Ala-Tyr-D-Trp-t-4-AchxAla-Thr-Phe);
cyclo(Pro-Tyr-D-Trp-4-Amphe-Thr-Phe);
cyclo(Pro-Phe-D-Trp-4-Amphe-Thr-Phe);
cyclo(N-Me-Ala-Tyr-D-Trp-4-Amphe-Thr-Phe);
cyclo(Asn-Phe-Phe-D-Trp-Lys-Thr-Phe-Gaba);
cyclo(Asn-Phe-Phe-D-Trp-Lys-Thr-Phe-Gaba-Gaba);
cyclo(Asn-Phe-D-Trp-Lys-Thr-Phe);
cyclo(Asn-Phe-Phe-D-Trp-Lys-Thr-Phe-NH(CH$_2$)$_4$CO);
cyclo(Asn-Phe-Phe-D-Trp-Lys-Thr-Phe-β-Ala);
cyclo(Asn-Phe-Phe-D-Trp-Lys-Thr-Phe-D-Glu)-OH;
cyclo(Phe-Phe-D-Trp-Lys-Thr-Phe);
cyclo(Phe-Phe-D-Trp-Lys-Thr-Phe-Gly);
cyclo(Phe-Phe-D-Trp-Lys-Thr-Phe-Gaba);
cyclo(Asn-Phe-Phe-D-Trp-Lys-Thr-Phe-Gly);
cyclo(Asn-Phe-Phe-D-Trp(F)-Lys-Thr-Phe-Gaba);
cyclo(Asn-Phe-Phe-D-Trp(NO$_2$)-Lys-Thr-Phe-Gaba);
cyclo(Asn-Phe-Phe-Trp(Br)-Lys-Thr-Phe-Gaba);
cyclo(Asn-Phe-Phe-D-Trp-Lys-Thr-Phe(I)-Gaba);
cyclo(Asn-Phe-Phe-D-Trp-Lys-Thr-Tyr(But)-Gaba);
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Tpo-Cys)-OH;
cyclo(Bmp-Lys-Asn-Phe-Phe-D-Trp-Lys-Thr-Phe-Thr-MeLeu-Cys)-OH;
cyclo(Phe-Phe-D-Trp-Lys-Thr-Phe-Phe-Gaba);
cyclo(Phe-Phe-D-Trp-Lys-Thr-Phe-D-Phe-Gaba);
cyclo(Phe-Phe-D-Trp(5F)-Lys-Thr-Phe-Phe-Gaba);
cyclo(Asn-Phe-Phe-D-Trp-Lys(Ac)-Thr-Phe-NH—(CH$_2$)$_3$—CO);
cyclo(Lys-Phe-Phe-D-Trp-Lys-Thr-Phe-Gaba);
cyclo(Lys-Phe-Phe-D-Trp-Lys-Thr-Phe-Gaba);
cyclo(Orn-Phe-Phe-D-Trp-Lys-Thr-Phe-Gaba); and
H-Cys-Phe-Phe-D-Trp-Lys-Thr-Phe-Cys-NH$_2$ (BIM-23268).

Note that for all somatostatin agonists described herein, each amino acid residue represents the structure of —NH—C(R)H—CO—, in which R is the side chain (e.g., CH$_3$ for Ala) except for Thr-ol which stands for —NH—CH(CH(CH$_3$)OH)—CH$_2$—OH and Pro which stands for —N—C(R')H—CO— where R' is —(CH$_2$)$_3$— attached to the α-nitrogen and α-carbon. Lines between amino acid residues represent peptide bonds which join the amino acids. Also, where the amino acid residue is optically active, it is the L-form configuration that is intended unless D-form is expressly designated. A disulfide bridge is formed between two Cys residues; however, it is not shown.

Use of linear somatostatin agonists of the following formula is also within the invention:

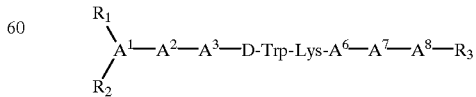

wherein
A$^1$ is a D- or L-isomer of Ala, Leu, Ile, Val, Nle, Thr, Ser, β-Nal, β-Pal, Trp, Phe, 2,4-dichloro-Phe, pentafluoro- Phe, p-X-Phe, or o-X-Phe, wherein X is $CH_3$, Cl, Br, F, OH, $OCH_3$ or $NO_2$;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^3$ is pyridyl-Ala, Trp, Phe, β-Nal, 2,4-dichloro-Phe, pentafluoro-Phe, o-X-Phe, or p-X-Phe, wherein X is $CH_3$, Cl, Br, F, OH, $OCH_3$ or $NO_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$;

each $R_1$ and $R_2$, independently, is H, lower acyl or lower alkyl; and $R_3$ is OH or $NH_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

Examples of linear agonists to be used in the method of this invention include:
H-D-Phe-p-chloro-Phe-Tyr-D-Trp-Lys-Thr-Phe-Thr-$NH_2$;
H-D-Phe-p-$NO_2$-Phe-Tyr-D-Trp-Lys-Val-Phe-Thr-$NH_2$;
H-D-Nal-p-chloro-Phe-Tyr-D-Trp-Lys-Val-Phe-Thr-$NH_2$;
H-D-Phe-Phe-Phe-D-Trp-Lys-Thr-Phe-Thr-$NH_2$ (BIM-23052);
H-D-Phe-Phe-Tyr-D-Trp-Lys-Val-Phe-Thr-$NH_2$;
H-D-Phe-p-chloro-Phe-Tyr-D-Trp-Lys-Val-Phe-Thr-$NH_2$; and
H-D-Phe-Ala-Tyr-D-Trp-Lys-Val-Ala-β-D-Nal-$NH_2$.

If desired, one or more chemical moieties, e.g., a sugar derivative, mono or poly-hydroxy $C_{2-12}$ alkyl, mono or poly-hydroxy $C_{2-12}$ acyl group, or a piperazine derivative, can be attached to the somatostatin agonist, e.g., to the N-terminus amino acid. See PCT Application WO 88/02756, European Application 0 329 295, and PCT Application No. WO 94/04752. An example of a somatostatin agonists which contain N-terminal chemical substitutions are:

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA., 89:251–255 (1992); SSTR-3 in Yamade, et al., Mol. Endocrinol. 6:2136–2142 (1993); and SSTR-4 and SSTR-5 in Yamada, et al., Biochem. Biophys. Res. Commun. 195:844–852 (1993)) and are also available from American Type Culture Collection (ATCC, Rockville, Md.) (ATCC Nos. 79044 (SSTR-1), 79046 (SSTR-2), and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual*, CSHL, 1982). Restriction endonucleases are available from New England Biolabs (Beverly, Mass.). This cDNA fragment was inserted into the mammalian expression vector, pCMV (Russell, D., et al., J. Biol. Chem., 264:8222–8229 (1989)), using standard molecular biology techniques (see e.g., Maniatis, T., et al., Molecular Cloning,—A Laboratory Manual, Cold Spring Harbor Laboratory, 1982) to produce the expression plasmid, pCMV-human SSTR-1 through pCMV-human SSTR-5. Other mammalian expression vectors include pcDNA1/Amp (Invitrogen, Sandlesy, Calif.). The expression plasmids were introduced into the suitable bacterial host, *E. Coli* HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density $1×10^6$/60-cm plate (Baxter Scientific Products, McGaw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for

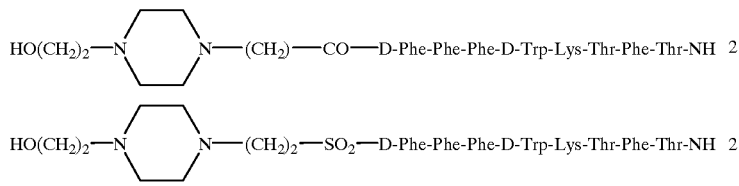

Synthesis of Somatostatin Agonists

The methods for synthesizing somatostatin agonists is well documented and are within the ability of a person of ordinary skill in the art.

Synthesis of short amino acid sequences is well established in the peptide art. For example, synthesis of H-D-Phe-Phe-Phe-D-Trp-Lys-Thr-Phe-Thr-$NH_2$, described above, can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and PCT Publication No. WO 94/04752.

growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2, Cold Spring Harbor Laboratory, Cold Spring Harbor, N.Y., 1989) and by receptor binding using [$^{125}$I-Tyr$^{11}$] somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0–4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$]somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter were then washed three times with 5 ml aliquots of ice-cold buffer. Specific binding was defined as the total [$^{125}$I-Tyr$^{11}$] somatostatin-14 bound minus that bound in the presence of 1000 nM. The Ki values for the tested somatostatin agonists were calculated by using the following formula: $Ki=IC_{50}/[1+(LC/LEC)]$ where $IC_{50}$ is the concentration of test somatostatin agonist required to inhibit 50 percent of the specific binding of the radioligand [$^{125}$I-Tyr$^{11}$]somatostatin-14, LC is the concentration of the radioligand (0.05 nM), and LEC is the equilibrium dissociation constant of the radioligand (0.16 nM). The Ki values for the tested somatostatin and somatostatin agonists are shown in Table I.

TABLE I

|  | hSSTR-1 | hSSTR-2 | hSSTR-3 | hSSTR-4 | hSSTR-5 |
|---|---|---|---|---|---|
| Somatostatin-14 | 2.256 | 0.71 | 1.432 | 1.768 | 0.883 |
| Somatostatin-28 | 2.382 | 0.57 | 1.021 | 7.93 | 0.383 |
| BIM-23052 | 97.64 | 5.77 | 5.586 | 126.5 | 1.227 |
| BM-23268 | 12.27 | 6.84 | 61.55 | 19.96 | 0.376 |

Survival of Transplanted Pancreatic Cells

The somatostatin analogs which bind to a somatostatin receptor may be further tested for their ability to prolong the functional life of transplanted pancreatic islet cells following procedures set forth below or similar procedures.
(a) Syngeneic Islet Transplantation in Rats Rats are made diabetic through the administration of streptozotocin or alloxan (Sigma, St. Louis, Mo.), which destroys the insulin-secreting β-islet cells of the rat pancreas (Mallaise, W. J., et al., Proc. Natl. Acad. Sci. USA 79:927–930 (1982); and Junod, A., et al., Proc. Soc. Exp. Biol. Med. 126:201–205 (1967)). Rat pancreatic islets, previously prepared, are then implanted into the diabetic rats (e.g., under the rat's kidney capsule). The function of the transplanted islets is periodically assessed by measuring the insulin response to a glucose challenge. The ability of a somatostatin receptor-binding compound to extend the functional life of the transplanted cells is determined by comparing the insulin response to hyperglycemia between groups of treated and untreated animals over a period of time, wherein the treated group is administered with the test compound subcutaneously (e.g., single daily injection or continuously via infusion pump and sustained release formulation).

(b) Human β-Islet Xenografts in Non-Immunocompetent Mice

The somatostatin agonists may also be tested directly on human pancreatic islets. Isolated human pancreatic islets are transplanted into athymic mice (e.g., under the kidney capsule), and the mice are subsequently made diabetic by the administration of alloxan. Transplanted human pancreatic islets are resistant to alloxan treatment, while the endogenous pancreatic cells of the recipient animal are destroyed (Eizirik, et al., Proc. Natl. Acad. Sci. USA 91:9253–9256, (1994)). The function of the transplanted islets is periodically assessed by measuring the insulin response to a glucose challenge. The ability of a somatostatin receptor-binding compound to extend the functional life of the transplanted cells is determined by comparing the insulin response to hyperglycemia between groups of somatostatin treated and untreated animals over a period of time, wherein the treated group is administered with the test compound somatostatin subcutaneously (e.g., single daily injection or continuously via infusion pump or sustained release formulation).

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of prolonging the survival of pancreatic cells transplanted in a patient said method comprising administering a therapeutically effective amount of a somatostatin agonist selected from the group consisting of D-β-Nal-Cys-Tyr-D-Trp-Lys-Thr-Cys-Thr-$NH_2$,
D-Phe-Cys-Phe-D-Trp-Lys-Thr-Cys-β-Nal-$NH_2$,
D-Phe-Cys-Tyr-D-Trp-Lys-Thr-Cys-β-Nal-$NH_2$,
D-β-Nal-Cys-Phe-D-Trp-Lys-Thr-Cys-Thr-$NH_2$,
D-Phe-Cys-Tyr-D-Trp-Lys-Thr-Pen-Thr-$NH_2$,
D-Phe-Cys-Phe-D-Trp-Lys-Thr-Pen-Thr-$NH_2$,
D-Phe-Cys-Tyr-D-Trp-Lys-Thr-Pen-Thr-OH,
D-Phe-Cys-Phe-D-Trp-Lys-Thr-Pen-Thr-OH,
Gly-Pen-Phe-D-Trp-Lys-Thr-Cys-Thr-OH,
Phe-Pen-Tyr-D-Trp-Lys-Thr-Cys-Thr-OH,
Phe-Pen-Phe-D-Trp-Lys-Thr-Pen-Thr-OH,
H-D-Phe-Cys-Phe-D-Trp-Lys-Thr-Cys-Thr-ol,
H-D-Phe-Cys-Phe-D-Trp-Lys-Thr-Cys-Thr-$NH_2$,
H-D-Trp-Cys-Tyr-D-Trp-Lys-Val-Cys-Thr-$NH_2$,
H-D-Trp-Cys-Phe-D-Trp-Lys-Thr-Cys-Thr-$NH_2$,
H-D-Phe-Cys-Tyr-D-Trp-Lys-Val-Cys-Thr-$NH_2$,
H-D-Phe-Cys-Tyr-D-Trp-Lys-Val-Cys-Trp-$NH_2$,
H-D-Phe-Cys-Tyr-D-Trp-Lys-Val-Cys-Thr-$NH_2$,
Ac-D-Phe-Lys*-Tyr-D-Trp-Lys-Val-Asp-Thr-$NH_2$ (an amide bridge formed between Lys* and Asp),
Ac-hArg(Et)$_2$-Gly-Cys-Phe-D-Trp-Lys-Thr-Cys-Thr-$NH_2$,
Ac-D-hArg(Et)$_2$-Gly-Cys-Phe-D-Trp-Lys-Thr-Cys-Thr-$NH_2$,
Ac-D-hArg(Bu)-Gly-Cys-Phe-D-Trp-Lys-Thr-Cys-Thr-$NH_2$,
Ac-D-hArg(Et)$_2$-Cys-Phe-D-Trp-Lys-Thr-Cys-Thr-$NH_2$,
Ac-L-hArg(Et)$_2$-Cys-Phe-D-Trp-Lys-Thr-Cys-Thr-$NH_2$,
Ac-D-hArg($CH_2CF_3$)$_2$-Cys-Phe-D-Trp-Lys-Thr-Cys-Thr-$NH_2$,
Ac-D-hArg($CH_2CF_3$)$_2$-Gly-Cys-Phe-D-Trp-Lys-Thr-Cys-Thr-$NH_2$,
Ac-D-hArg($CH_2CF_3$)$_2$-Gly-Cys-Phe-D-Trp-Lys-Thr-Cys-Phe-$NH_2$,
Ac-D-hArg($CH_2CF_3$)$_2$-Gly-Cys-Phe-D-Trp-Lys-Thr-Cys-Thr-NHEt,
Ac-L-hArg($CH_2CF_3$)$_2$-Gly-Cys-Phe-D-Trp-Lys-Thr-Cys-Thr-$NH_2$,
Ac-D-hArg($CH_2CF_3$)$_2$-Gly-Cys-Phe-D-Trp-Lys(Me)-Thr-Cys-Thr-$NH_2$,
Ac-D-hArg($CH_2CF_3$)$_2$-Gly-Cys-Phe-D-Trp-Lys(Me)-Thr-Cys-Thr-NHEt,
Ac-hArg($CH_3$, hexyl)-Gly-Cys-Phe-D-Trp-Lys-Thr-Cys-Thr-$NH_2$,
H-hArg(hexyl$_2$)-Gly-Cys-Phe-D-Trp-Lys-Thr-Cys-Thr-$NH_2$,
Ac-D-hArg(Et)$_2$-Gly-Cys-Phe-D-Trp-Lys-Thr-Cys-Thr-NHEt,
Ac-D-hArg(Et)$_2$-Gly-Cys-Phe-D-Trp-Lys-Thr-Cys-Phe-$NH_2$,
Propionyl-D-hArg(Et)$_2$-Gly-Cys-Phe-D-Trp-Lys(iPr)-Thr-Cys-Thr-$NH_2$, Ac-D-β-Nal-Gly-Cys-Phe-D-Trp-Lys-Thr-Cys-Gly-hArg(Et)₂-NH₂,
Ac-D-Lys(iPr)-Gly-Cys-Phe-D-Trp-Lys-Thr-Cys-Thr-NH₂,
Ac-D-hArg(CH₂CF₃)₂-D-hArg(CH₂CF₃)₂-Gly-Cys-Phe-D-Trp-Lys-Thr-Cys-Thr-NH₂,
Ac-D-hArg(CH₂CF₃)₂-D-hArg(CH₂CF₃)₂-Gly-Cys-Phe-D-Trp-Lys-Thr-Cys-Phe-NH₂,
Ac-D-hArg(Et)₂-D-hArg(Et)₂-Gly-Cys-Phe-D-Trp-Lys-Thr-Cys-Thr-NH₂,
Ac-Cys-Lys-Asn-4-Cl-Phe-Phe-D-Trp-Lys-Thr-Phe-Thr-Ser-D-Cys-NH₂,
Bmp-Tyr-D-Trp-Lys-Val-Cys-Thr-NH₂,
Bmp-Tyr-D-Trp-Lys-Val-Cys-Phe-NH₂,
Bmp-Tyr-D-Trp-Lys-Val-Cys-p-Cl-Phe-NH₂,
Bmp-Tyr-D-Trp-Lys-Val-Cys-β-Nal-NH₂,
H-D-β-Nal-Cys-Tyr-D-Trp-Lys-Val-Cys-Thr-NH₂,
H-D-Phe-Cys-Tyr-D-Trp-Lys-Abu-Cys-Thr-NH₂,
H-D-Phe-Cys-Tyr-D-Trp-Lys-Abu-Cys-β-Nal-NH₂,
H-pentafluoro-D-Phe-Cys-Tyr-D-Trp-Lys-Val-Cys-Thr-NH₂,
Ac-D-β-Nal-Cys-pentafluoro-Phe-D-Trp-Lys-Val-Cys-Thr-NH₂,
H-D-β-Nal-Cys-Tyr-D-Trp-Lys-Val-Cys-β-Nal-NH₂,
H-D-Phe-Cys-Tyr-D-Trp-Lys-Val-Cys-β-Nal-NH₂,
H-D-β-Nal-Cys-Tyr-D-Trp-Lys-Abu-Cys-Thr-NH₂,
H-D-p-Cl-Phe-Cys-Tyr-D-Trp-Lys-Abu-Cys-Thr-NH₂,
Ac-D-p-Cl-Phe-Cys-Tyr-D-Trp-Lys-Abu-Cys-Thr-NH₂,
H-D-Phe-Cys-β-Nal-D-Trp-Lys-Val-Cys-Thr-NH₂,
H-D-Phe-Cys-Tyr-D-Trp-Lys-Cys-Thr-NH₂,
cyclo(Pro-Phe-D-Trp-N-Me-Lys-Thr-Phe),
cyclo(Pro-Phe-D-Trp-N-Me-Lys-Thr-Phe),
cyclo(Pro-Phe-D-Trp-Lys-Thr-N-Me-Phe),
cyclo(N-Me-Ala-Tyr-D-Trp-Lys-Thr-Phe),
cyclo(Pro-Tyr-D-Trp-Lys-Thr-Phe),
cyclo(Pro-Phe-D-Trp-Lys-Thr-Phe),
cyclo(Pro-Phe-L-Trp-Lys-Thr-Phe),
cyclo(Pro-Phe-D-Trp(F)-Lys-Thr-Phe),
cyclo(Pro-Phe-Trp(F)-Lys-Thr-Phe),
cyclo(Pro-Phe-D-Trp-Lys-Ser-Phe),
cyclo(Pro-Phe-D-Trp-Lys-Thr-p-Cl-Phe),
cyclo(D-Ala-N-Me-D-Phe-D-Thr-D-Lys-Trp-D-Phe),
cyclo(D-Ala-N-Me-D-Phe-D-Val-Lys-D-Trp-D-Phe),
cyclo(D-Ala-N-Me-D-Phe-D-Thr-Lys-D-Trp-D-Phe),
cyclo(D-Abu-N-Me-D-Phe-D-Val-Lys-D-Trp-D-Tyr),
cyclo(Pr-Tyr-D-Trp-t-4-AchxAla-Thr-Phe),
cyclo(Pro-Phe-D-Trp-t-4-AchxAla-Thr-Phe),
cyclo(N-Me-Ala-Tyr-D-Trp-Lys-Val-Phe),
cyclo(N-Me-Ala-Tyr-D-Trp-t-4-AchxAla-Thr-Phe),
cyclo(Pro-Tyr-D-Trp-4-Amphe-Thr-Phe),
cyclo(Pro-Phe-D-Trp-4-Amphe-Thr-Phe),
cyclo(N-Me-Ala-Tyr-D-Trp-4-Amphe-Thr-Phe),
cyclo(Asn-Phe-Phe-D-Trp-Lys-Thr-Phe-Gaba),
cyclo(Asn-Phe-Phe-D-Trp-Lys-Thr-Phe-Gaba-Gaba),
cyclo(Asn-Phe-D-Trp-Lys-Thr-Phe),
cyclo(Asn-Phe-Phe-D-Trp-Lys-Thr-Phe-NH(CH₂)₄CO),
cyclo(Asn-Phe-Phe-D-Trp-Lys-Thr-Phe-β-Ala),
cyclo(Asn-Phe-Phe-D-Trp-Lys-Thr-Phe-D-Glu)-OH,
cyclo(Phe-Phe-D-Trp-Lys-Thr-Phe),
cyclo(Phe-Phe-D-Trp-Lys-Thr-Phe-Gly),
cyclo(Phe-Phe-D-Trp-Lys-Thr-Phe-Gaba),
cyclo(Asn-Phe-Phe-D-Trp-Lys-Thr-Phe-Gly),
cyclo(Asn-Phe-Phe-D-Trp(F)-Lys-Thr-Phe-Gaba),
cyclo(Asn-Phe-Phe-D-Trp(NO₂)-Lys-Thr-Phe-Gaba),
cyclo(Asn-Phe-Phe-Trp(Br)-Lys-Thr-Phe-Gaba),
cyclo(Asn-Phe-Phe-D-Trp-Lys-Thr-Phe(I)-Gaba),
cyclo(Asn-Phe-Phe-D-Trp-Lys-Thr-Tyr(But)-Gaba),
cyclo(Bmp-Lys-Asn-Phe-Phe-D-Trp-Lys-Thr-Phe-Thr-Pro-Cys)-OH,
cyclo(Bmp-Lys-Asn-Phe-Phe-D-Trp-Lys-Thr-Phe-Thr-Pro-Cys)-OH,
cyclo(Bmp-Lys-Asn-Phe-Phe-D-Trp-Lys-Thr-Phe-Thr-Tpo-Cys)-OH,
cyclo(Bmp-Lys-Asn-Phe-Phe-D-Trp-Lys-Thr-Phe-Thr-MeLeu-Cys)-OH,
cyclo(Phe-Phe-D-Trp-Lys-Thr-Phe-Phe-Gaba),
cyclo(Phe-Phe-D-Trp-Lys-Thr-Phe-D-Phe-Gaba),
cyclo(Phe-Phe-D-Trp(5F)-Lys-Thr-Phe-Phe-Gaba),
cyclo(Asn-Phe-Phe-D-Trp-Lys(Ac)-Thr-Phe-NH—(CH₂)₃—CO),
cyclo(Lys-Phe-Phe-D-Trp-Lys-Thr-Phe-Gaba),
cyclo(Lys-Phe-Phe-D-Trp-Lys-Thr-Phe-Gaba),
cyclo(Orn-Phe-Phe-D-Trp-Lys-Thr-Phe-Gaba) and
H-Cys-Phe-Phe-D-Trp-Lys-Thr-Phe-Cys-NH₂
wherein a disulfide bond exists in the somatostatin agonists having two Cys residues.

2. A method of prolonging the survival of pancreatic cells transplanted in a patient said method comprising administering a therapeutically effective amount of a somatostatin agonist selected from the group consisting of the formula:

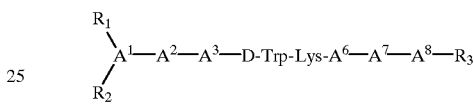

wherein

A¹ is a D- or L-isomer of Ala, Leu, Ile, Val, Nle, Thr, Ser, -Nal, -Pal, Trp, Phe, 2,4-dichloro-Phe, pentafluoro-Phe, p-X-Phe, or o-X-Phe, wherein X is CH₃, Cl, Br, F, OH, OCH₃ or NO₂;

A² is Ala, Leu, Ile, Val, Nle, Phe, -Nal, pyridyl-Ala, Trp, 2,4-dichloro-Phe, pentafluoro-Phe, o-X-Phe, or p-X-Phe, wherein X is CH₃, Cl, Br, F, OH, OCH₃ or NO₂;

A³ is pyridyl-Ala, Trp, Phe, -Nal, 2,4-dichloro-Phe, pentafluoro-Phe, o-X-Phe, or p-X-Phe, wherein X is CH₃, Cl, Br, F, OH, OCH₃ or NO₂;

A⁶ is Val, Ala, Leu, Ile, Nle, Thr, Abu, or Ser;

A⁷ is Ala, Leu, Ile, Val, Nle, Phe, -Nal, pyridyl-Ala, Trp, 2,4-dichloro-Phe, pentafluoro-Phe, o-X-Phe, or p-X-Phe, wherein X is CH₃, Cl, Br, F, OH, OCH₃ or NO₂;

A⁸ is a D- or L-isomer of Ala, Leu, Ile, Val, Nle, Thr, Ser, Phe, -Nal, pyridyl-Ala, Trp, 2,4-dichloro-Phe, pentafluoro-Phe, p-X-Phe, or o-X-Phe, wherein X is CH₃, Cl, Br, F, OH, OCH₃ or NO₂;

each R₁ and R₂, independently, is H, lower acyl or lower alkyl; and R₃ is OH or NH₂; provided that either A¹ or A⁸ or both must be an aromatic amino acid and that either A², or A⁷ or both must also be an aromatic amino acid; however A¹, A², A⁷ and A⁸ cannot all be aromatic amino acids in said somatostatin agonist.

3. A method according to claim 2 wherein said somatostatin agonist is selected from the group consisting of
H-D-Phe-p-chloro-Phe-Tyr-D-Trp-Lys-Thr-Phe-Thr-NH₂,
H-D-Phe-p-NO₂-Phe-Tyr-D-Trp-Lys-Val-Phe-Thr-NH₂,
H-D-Nal-p-chloro-Phe-Tyr-D-Trp-Lys-Val-Phe-Thr-NH₂,
H-D-Phe-Phe-Phe-D-Trp-Lys-Thr-Phe-Thr-NH₂,
H-D-Phe-Phe-Tyr-D-Trp-Lys-Val-Phe-Thr-NH₂,
H-D-Phe-p-chloro-Phe-Tyr-D-Trp-Lys-Val-Phe-Thr-NH₂, and
H-D-Phe-Ala-Tyr-D-Trp-Lys-Val-Ala- -D-Nal-NH₂.

4. A method of prolonging the survival of pancreatic cells transplanted in a patient said method comprising administering a therapeutically effective amount of a somatostatin agonist selected from the group consisting of

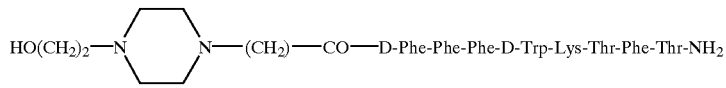

and

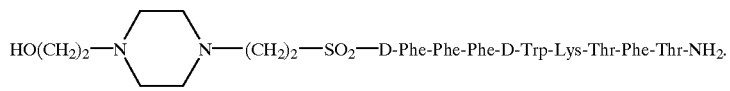

5. A method according to claim 1 wherein said pancreatic cells are in a pancreatic islet.

6. A method according to claim 2 wherein said pancreatic cells are in a pancreatic islet.

7. A method according to claim 3 wherein said pancreatic cells are in a pancreatic islet.

8. A method according to claim 4 wherein said pancreatic cells are in a pancreatic islet.

9. A method according to claim 1 wherein said pancreatic cells are allograft cells.

10. A method according to claim 2 wherein said pancreatic cells are allograft cells.

11. A method according to claim 3 wherein said pancreatic cells are allograft cells.

12. A method according to claim 4 wherein said pancreatic cells are allograft cells.

13. A method according to claim 1 wherein said patient is an insulin dependent diabetic.

14. A method according to claim 2 wherein said patient is an insulin dependent diabetic.

15. A method according to claim 3 wherein said patient is an insulin dependent diabetic.

16. A method according to claim 4 wherein said patient is an insulin dependent diabetic.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 6 amino acids
      (B) TYPE: amino acid
      (C) STRANDEDNESS: Not Relevant
      (D) TOPOLOGY: circular (ii) MOLECULE TYPE: peptide (xi) SEQUENCE DESCRIPTION: SEQ ID NO: 1:

```
Pro Phe Trp Lys Thr Phe
1               5
```

(2) INFORMATION FOR SEQ ID NO: 2:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: circular (ii) MOLECULE TYPE: peptide (ix) FEATURE:
        (D) OTHER INFORMATION: wherein Xaa at position 3 is
            5-fluoro-tryptophan (xi) SEQUENCE DESCRIPTION: SEQ ID NO: 2:

```
Pro Phe Xaa Lys Thr Phe
1               5
```

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: circular (ii) MOLECULE TYPE: peptide (ix) FEATURE:
        (D) OTHER INFORMATION: wherein Xaa at position 4 is 5-bromo-
            tryptophan, and Xaa at position 8 is 4-aminobutyric acid.

(xi) SEQUENCE DESCRIPTION: SEQ ID NO: 3:

```
Asn Phe Phe Xaa Lys Thr Phe Xaa
1               5
```